US008489409B2

(12) United States Patent
Moussavi et al.

(10) Patent No.: US 8,489,409 B2
(45) Date of Patent: Jul. 16, 2013

(54) AUTOMATED NEWBORN SCREENING RESULTS REPORTING

(75) Inventors: Mahcameh Moussavi, Lenexa, KS (US); Mark A. Hoffman, Lees Summit, MO (US)

(73) Assignee: Cerner Innovation, Inc., Overland Park, KS (US)

( * ) Notice: Subject to any disclaimer, the term of this patent is extended or adjusted under 35 U.S.C. 154(b) by 1717 days.

(21) Appl. No.: 11/380,459

(22) Filed: Apr. 27, 2006

(65) Prior Publication Data

US 2007/0255585 A1    Nov. 1, 2007

(51) Int. Cl.
*G06Q 10/00* (2012.01)

(52) U.S. Cl.
USPC .................................. 705/2; 705/3

(58) Field of Classification Search
USPC ............................................................. 705/2
See application file for complete search history.

(56) References Cited

U.S. PATENT DOCUMENTS

| | | | |
|---|---|---|---|
| 4,315,309 A | | 2/1982 | Coli |
| 5,924,074 A | | 7/1999 | Evans |
| 6,018,713 A | * | 1/2000 | Coli et al. ........................ 705/2 |
| 6,581,012 B1 | * | 6/2003 | Aryev et al. .................... 702/22 |
| 7,567,913 B2 | | 7/2009 | Bennett et al. |
| 2002/0042725 A1 | | 4/2002 | Mayaud |
| 2002/0072934 A1 | | 6/2002 | Ross et al. |
| 2002/0169636 A1 | | 11/2002 | Eggers et al. |
| 2004/0010425 A1 | | 1/2004 | Wilkes et al. |
| 2004/0030578 A1 | * | 2/2004 | Cross et al. ....................... 705/2 |
| 2004/0199333 A1 | * | 10/2004 | Hoffman et al. ................ 702/20 |
| 2004/0260666 A1 | | 12/2004 | Pestotnik et al. |
| 2007/0294103 A1 | * | 12/2007 | Ahmad et al. .................... 705/2 |

OTHER PUBLICATIONS

Mordaunt, Virginia L. et al., "Computerized Assisted Management of a Regionalized Newborn Screening Program", 1988, Journal of Medical Systems, vol. 12, No. 2., pp. 77-88.*
Wolfson, Martin et al., "Postrelational Database for Newborn Screening and Tracking", Journal of Medical Systems, vol. 12, No. 2, 1988.*
Advisory Action mailed Sep. 8, 2009 in U.S. Appl. No. 11/424,187, filed Jun. 14, 2006.
Final Office Action mailed Jul. 7, 2009 in U.S. Appl. No. 11/424,187, filed Jun. 14, 2006.
NonFinal Office Action mailed Dec. 23, 2008 in U.S. Appl. No. 11/424,187, filed Jun. 14, 2006.
NonFinal Office Action of U.S. Appl. No. 11/424,187 mailed Dec. 28, 2009, 19 pages.

* cited by examiner

*Primary Examiner* — Michael Fuelling
(74) *Attorney, Agent, or Firm* — Shook Hardy & Bacon LLP (57) ABSTRACT

Systems and methods are provided for facilitating the electronic collection and dissemination of newborn screening results to identified and/or default recipients of the results. A newborn screening manager may be provided to receive and store newborn screening results in an associated database. The newborn screening results may then be communicated electronically to any number of recipients of the results. In some cases, a notification may be provided to the recipients, indicating that the newborn screening results are available to be reviewed. The recipients may then access and review the results.

16 Claims, 8 Drawing Sheets

Ellen Young
DOB: 9/15/05
Hospital of Birth: Memorial West

Enter newborn screening test results:

| Disorder | Protein | Result |
|---|---|---|
| Phenylketonuria (PKU) | (AA).PAH.0 | negative |
| Congenital adrenal hyperplasia (CAH) | (AA).CYP21A2.0 | negative |
| Galactosemia | (AA).GALT.0 | positive |
| Sickle cell disease | (AA).HBB.0 | |
| Medium-chain acyl-CoA dehydrogenase (MCAD) | (AA).ACADM.0 | |

Ready for supervisory review

[ COMPLETE ]
502

Physician: Dr. Smith

Lab Review Queue

| Patient | Order | Order Status | Supervisory Review |
|---|---|---|---|
| Nicole Jones | Newborn Screen | Pending | N/A |
| William Miller | Newborn Screen | Pending | N/A |
| John Smith | Newborn Screen | Pending | N/A |
| Ellen Young | Newborn Screen | Complete | Pending |
| David Albright | Newborn Screen | Complete | Pending |

WELCOME, DR. SMITH.

THE FOLLOWING RESULTS ARE AWAITING YOUR REVIEW:

| PATIENT | DATE OF RESULT | HOSPITAL |
|---|---|---|
| ! DOE, JANE | TODAY, TUE 9/20/05 | MEMORIAL WEST |
| SMITH, JOHN | MON 9/19/05 | MEMORIAL WEST |
| JONES, NICOLE | MON 9/19/05 | BASELINE EAST |
| MILLER, WILLIAM | SUN 9/18/05 | MEMORIAL WEST |

NEWBORN SCREENING TEST RESULTS
JANE DOE (CLICK FOR DEMOGRAPHIC INFORMATION)
DOB: 9/13/05
HOSPITAL OF BIRTH: MEMORIAL WEST

RESULTS:

| DISORDER | PROTEIN | RESULT |
|---|---|---|
| PHENYLKETONURIA (PKU) | (AA) PAH.0 | NEGATIVE |
| CONGENITAL ADRENAL HYPERPLASIA (CAH) | (AA) CYP21A2.0 | NEGATIVE |
| GALACTOSEMIA | (AA) GALT.0 | NEGATIVE |
| SICKLE CELL DISEASE | (AA) HBB.0 | NEGATIVE |
| MEDIUM-CHAIN ACYL-COA DEHYDROGENASE (MCAD) | (AA) ACADM.0 | POSITIVE |

SCREEN POSITIVE FOR MEDIUM-CHAIN ACYL-COA DEHYDROGENASE DEFICIENCY (MCAD).

TESTING BY TANDEM MASS SPECTROMETER INDICATED METABOLITE LEVELS SUGGESTIVE OF
MCAD. BABIES AND CHILDREN WITH MCAD MAY EXPERIENCE ACUTE ILLNESS OR SUDDEN DEATH WITH LITTLE OR NO WARNING AS THE RESULT OF PROLONGED FASTING.

IMMEDIATE CONFIRMATORY TESTING RECOMMENDED.

CLICK HERE FOR MORE INFORMATION ABOUT MCAD.

CLICK HERE FOR A LIST OF YOUR PREFERRED LABORATORIES.

PLEASE INDICATE YOU HAVE REVIEWED THE RESULTS:

VERIFY

AUTOMATED NEWBORN SCREENING RESULTS REPORTING

CROSS-REFERENCE TO RELATED APPLICATIONS

Not applicable.

STATEMENT REGARDING FEDERALLY SPONSORED RESEARCH OR DEVELOPMENT

Not applicable.

BACKGROUND

Many newborns die or are seriously debilitated each year from diseases and disorders that can be easily detected and treated before any severe, long-term damage occurs. Early detection and communication of critical results indicating the presence of such a disorder are vital to ensure timely treatment is provided to prevent any detrimental effects. Accordingly, each state attempts to test every newborn for a panel of disorders determined by the state. In addition, a number of private laboratories provide expanded screening for a variety of additional disorders. Generally, newborn screening currently entails collecting a blood sample from a newborn shortly after birth. The blood sample is then sent to a state laboratory and/or an independent laboratory for testing. The laboratory performs the testing and sends the results to any indicated recipient, such as a pediatrician for the newborn or the hospital that served as the place of birth. Currently, reporting entails manually mailing, faxing, or phoning the newborn screening results to the recipients.

Although current newborn screening programs provide substantial benefit in detecting disorders and saving newborn lives, there remains a deficit. Nationally, 4,000 newborns are diagnosed with conditions screened for in newborn screening programs. However, it is estimated that 4.5% of screen-positive results are not successfully communicated to the proper recipient, resulting in a lack of confirmatory testing and appropriate medical follow-up for these at-risk infants. As mentioned above, current reporting entails manually mailing, faxing, or phoning of results to recipients. Recipients who do not receive results in a timely manner often assume that the results for the given newborn are normal. In addition, some recipients in highly populated areas have difficulty obtaining results for their patients if they do not have privileges at the hospital of birth. Simply, there is currently no automated approach to ensuring that recipients receive newborn screening results.

BRIEF SUMMARY

This summary is provided to introduce a selection of concepts in a simplified form that are further described below in the Detailed Description. This summary is not intended to identify key features or essential features of the claimed subject matter, nor is it intended to be used as an aid in determining the scope of the claimed subject matter.

Embodiments of the present invention relate to coordinating the collection and dissemination of newborn screening results. Accordingly, in one aspect, the present invention is directed to a method in a clinical computing environment for communicating a newborn screening result to one or more recipients. The method includes receiving a newborn screening result at a newborn screening manager, wherein the newborn screening manager is configured to communicate with at least one of a state laboratory performing newborn screening and a state office responsible for coordinating newborn screening results. The method also includes identifying one or more recipients of the newborn screening result. The method further includes communicating the newborn screening result to the one or more recipients.

In another aspect of the invention, an embodiment is directed to a method in a clinical computing environment for facilitating the notification of an availability of a newborn screening result. The method includes receiving a newborn screening result and adding the newborn screening result to a list of newborn screening results pending review. The method also includes providing a notification of an availability of the newborn screening result to one or more recipients. The method further includes providing the list of newborn screening results pending review to at least one of a state laboratory performing newborn screening and a state office responsible for coordinating newborn screening results.

In yet another aspect, an embodiment of the present invention is directed to a system in a clinical computing environment for facilitating the communication of newborn screening results. The system includes a first interface to one or more sources of newborn screening results. The system also includes a second interface to one or more recipients of newborn screening results. The system further includes a newborn screening manager communicating with the one or more sources of newborn screening results via the first interface and with the one or more recipients via the second interface. The newborn screening manager is configured to access one or more newborn screening results from the one or more sources of newborn screening results, determine at least one of the one or more recipients for receiving at least one of the one or more newborn screening results, and communicate the at least one newborn screening results to the at least one recipient.

BRIEF DESCRIPTION OF THE SEVERAL VIEWS OF THE DRAWINGS

The present invention is described in detail below with reference to the attached drawing figures, wherein.

DETAILED DESCRIPTION

The subject matter of the present invention is described with specificity herein to meet statutory requirements. However, the description itself is not intended to limit the scope of this patent. Rather, the inventors have contemplated that the claimed subject matter might also be embodied in other ways, to include different steps or combinations of steps similar to the ones described in this document, in conjunction with other present or future technologies. Moreover, although the terms "step" and/or "block" may be used herein to connote different components of methods employed, the terms should not be interpreted as implying any particular order among or between various steps herein disclosed unless and except when the order of individual steps is explicitly described.

Embodiments of the present invention provide computerized systems and methods for electronically collecting newborn screening results and providing for the automatic dissemination of results to intended recipients. In some embodiments, a newborn screening manager may be provided for receiving newborn screening results and ensuring that the results are communicated to the proper recipients. Communication of the results may in some cases entail providing a notification of the availability of results to recipients and requiring the recipients to access the results and verify review of the results. A list of results pending review by recipients may also be provided to an entity responsible for distributing the results to recipients, such as a testing laboratory or state office, thereby providing a mechanism for ensuring that recipients receive and review the results.

Figure 1:
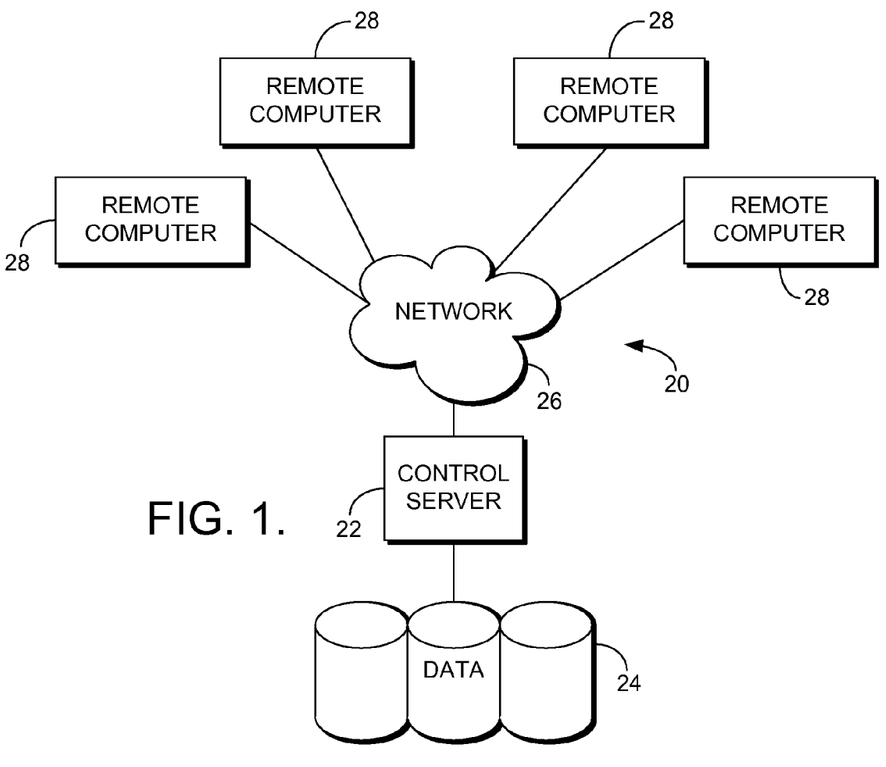
FIG. 1 is a block diagram of an exemplary computing environment suitable for use in implementing the present invention.

Referring to the drawings in general, and initially to FIG. 1 in particular, an exemplary computing system environment, for instance, a medical information computing system, on which embodiments of the present invention may be implemented is illustrated and designated generally as reference numeral 20. It will be understood and appreciated by those of ordinary skill in the art that the illustrated medical information computing system environment 20 is merely an example of one suitable computing environment and is not intended to suggest any limitation as to the scope of use or functionality of the invention. Neither should the medical information computing system environment 20 be interpreted as having any dependency or requirement relating to any single component or combination of components illustrated therein.

The present invention may be operational with numerous other general purpose or special purpose computing system environments or configurations. Examples of well-known computing systems, environments, and/or configurations that may be suitable for use with the present invention include, by way of example only, personal computers, server computers, hand-held or laptop devices, multiprocessor systems, microprocessor-based systems, set top boxes, programmable consumer electronics, network PCs, minicomputers, mainframe computers, distributed computing environments that include any of the above-mentioned systems or devices, and the like.

The present invention may be described in the general context of computer-executable instructions, such as program modules, being executed by a computer. Generally, program modules include, but are not limited to, routines, programs, objects, components, and data structures that perform particular tasks or implement particular abstract data types. The present invention may also be practiced in distributed computing environments where tasks are performed by remote processing devices that are linked through a communications network. In a distributed computing environment, program modules may be located in local and/or remote computer storage media including, by way of example only, memory storage devices.

With continued reference to FIG. 1, the exemplary medical information computing system environment 20 includes a general purpose computing device in the form of a server 22. Components of the server 22 may include, without limitation, a processing unit, internal system memory, and a suitable system bus for coupling various system components, including database cluster 24, with the server 22. The system bus may be any of several types of bus structures, including a memory bus or memory controller, a peripheral bus, and a local bus, using any of a variety of bus architectures. By way of example, and not limitation, such architectures include Industry Standard Architecture (ISA) bus, Micro Channel Architecture (MCA) bus, Enhanced ISA (EISA) bus, Video Electronic Standards Association (VESA) local bus, and Peripheral Component Interconnect (PCI) bus, also known as Mezzanine bus.

The server 22 typically includes, or has access to, a variety of computer readable media, for instance, database cluster 24. Computer readable media can be any available media that may be accessed by server 22, and includes volatile and nonvolatile media, as well as removable and non-removable media. By way of example, and not limitation, computer readable media may include computer storage media and communication media. Computer storage media may include, without limitation, volatile and nonvolatile media, as well as removable and nonremovable media implemented in any method or technology for storage of information, such as computer readable instructions, data structures, program modules, or other data. In this regard, computer storage media may include, but is not limited to, RAM, ROM, EEPROM, flash memory or other memory technology, CD-ROM, digital versatile disks (DVDs) or other optical disk storage, magnetic cassettes, magnetic tape, magnetic disk storage, or other magnetic storage device, or any other medium which can be used to store the desired information and which may be accessed by the server 22. Communication media typically embodies computer readable instructions, data structures, program modules, or other data in a modulated data signal, such as a carrier wave or other transport mechanism, and may include any information delivery media. As used herein, the term "modulated data signal" refers to a signal that has one or more of its attributes set or changed in such a manner as to encode information in the signal. By way of example, and not limitation, communication media includes wired media such as a wired network or direct-wired connection, and wireless media such as acoustic, RF, infrared, and other wireless media. Combinations of any of the above also may be included within the scope of computer readable media.

The computer storage media discussed above and illustrated in FIG. 1, including database cluster 24, provide storage of computer readable instructions, data structures, programs modules, and other data for the server 22.

The server 22 may operate in a computer network 26 using logical connections to one or more remote computers 28. Remote computers 28 may be located at a variety of locations in a medical or research environment, for example, but not limited to, clinical laboratories, hospitals and other inpatient settings, veterinary environments, ambulatory settings, medical billing and financial offices, hospital administration settings, home health care environments, and clinicians' offices. Clinicians may include, but are not limited to, a treating physician or physicians, specialists such as surgeons, radiologists, cardiologists, and oncologists, emergency medical technicians, physicians' assistants, nurse practitioners, nurses, nurses' aides, pharmacists, dieticians, microbiologists, laboratory experts, genetic counselors, researchers, veterinarians, students, and the like. The remote computers 28 may also be physically located in non-traditional medical care environments so that the entire health care community may be capable of integration on the network. The remote computers 28 may be personal computers, servers, routers, network PCs, peer devices, other common network nodes, or the like, and may include some or all of the components described above in relation to the server 22. The devices can be personal digital assistants or other like devices.

Exemplary computer networks 26 may include, without limitation, local area networks (LANs) and/or wide area networks (WANs). Such networking environments are commonplace in offices, enterprise-wide computer networks, intranets, and the Internet. When utilized in a WAN networking environment, the server 22 may include a modem or other means for establishing communications over the WAN, such as the Internet. In a networked environment, program modules or portions thereof may be stored in the server 22, in the database cluster 24, or on any of the remote computers 28. For example, and not by way of limitation, various application programs may reside on the memory associated with any one or more of the remote computers 28. It will be appreciated by those of ordinary skill in the art that the network connections shown are exemplary and other means of establishing a communications link between the computers (e.g., server 22 and remote computers 28) may be utilized.

In operation, a user may enter commands and information into the server 22 or convey the commands and information to the server 22 via one or more of the remote computers 28 through input devices, such as a keyboard, a pointing device (commonly referred to as a mouse), a trackball, or a touch pad. Other input devices may include, without limitation, microphones, satellite dishes, scanners, or the like. Commands and information may also be sent directly from a remote healthcare device to the server 22. In addition to a monitor, the server 22 and/or remote computers 28 may include other peripheral output devices, such as speakers and a printer.

Although many other internal components of the server 22 and the remote computers 28 are not shown, those of ordinary skill in the art will appreciate that such components and their interconnection are well known. Accordingly, additional details concerning the internal construction of the server 22 and the remote computers 28 are not further disclosed herein.

Figure 2:
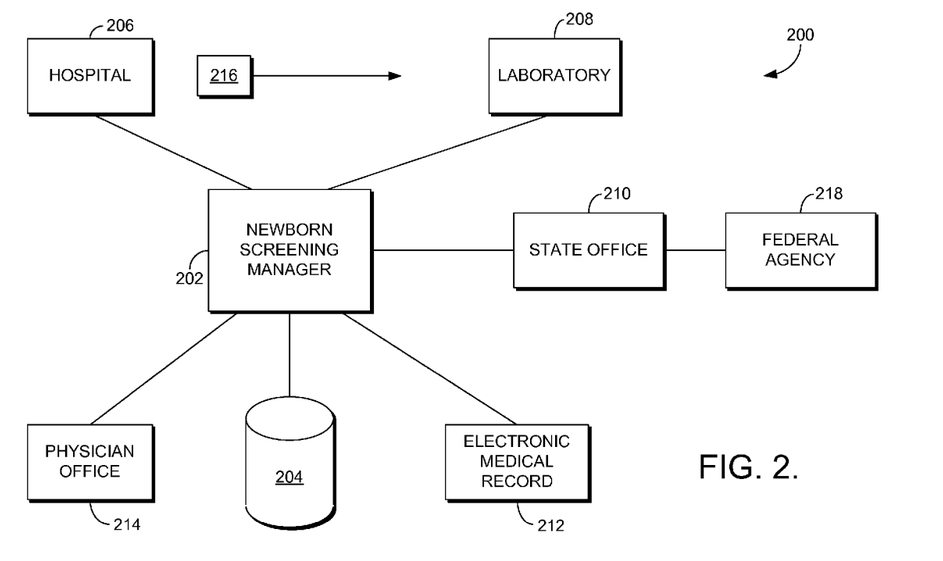
FIG. 2 is a block diagram showing an exemplary architecture for facilitating the collection and notification of newborn screening results in accordance with an embodiment of the present invention.

Referring now to FIG. 2, a block diagram is provided illustrating an exemplary architecture 200 for facilitating notification of newborn screening results in accordance with an embodiment of the present invention. As shown in FIG. 2, a newborn screening manager 202 may be provided to coordinate, among other things, the collection and dissemination of newborn screening results. The newborn screening manager 202 acts as a central repository for storing a multitude of newborn screening results. Newborn screening results and other information may be maintained in an associated database 204. After obtaining newborn screening results, the newborn screening manager 202 may provide a notification of the availability of the results to recipients indicated for individual results. Recipients may then access the available newborn screening results from the newborn screening manager 202. In addition, the newborn screening manager 202 may facilitate ensuring that recipients receive newborn screening results by allowing an entity, such as a laboratory providing results or a state office, for example, to review a list of results pending review by a recipient.

As shown in FIG. 2, the newborn screening manager 202 may be capable of communicating with a number of different entities, such as a hospital 206, a laboratory 208, a state office 210, an electronic medical record 212, and a physician office 214, for example, for the collection and dissemination of newborn screening results. It should be noted that the entities shown communicating with the newborn screening manager 202 in FIG. 2 are provided by way of example only and are not intended to limit the scope of the present invention in any way. Each entity may have a computing device, such as a remote computer 28 of FIG. 1, for communicating with the newborn screening manager 202. In addition, communication between the newborn screening manager 202 and the various entities may be via one or more networks, which may comprise one or more wide area networks (WANs) and one or more local area networks (LANs), as well as one or more public networks, such as the Internet, and one or more private networks. Further, entities may be able to access the newborn screening manager 202 in a variety of ways within the scope of the present invention. For example, in some embodiments, an entity may have a native clinical computing system, which may be able to communicate with the newborn screening manager 202. In other embodiments, a client application associated with the newborn screening manager 202 may reside on an entity's computing device facilitating communication with the newborn screening manager 202. In further embodiments, communication may simply be a web-based communication, using, for example, a web browser to access the newborn screening manager 202 via the Internet. Any and all such variations are contemplated to be within the scope of embodiments of the present invention.

In operation, at least one physical specimen 216 (e.g., a blood sample from a heel stick) is collected from a newborn within a specified timeframe after birth. Typically, this will be performed at the place of birth, which is often a hospital or other healthcare facility, such as the hospital 206 shown in FIG. 2. The physical specimen 216 is typically identified by some means, such as an identification number or barcode, for example. In some embodiments, an order for a newborn screening may be created in the newborn screening manager 202 at the time of collection of the physical specimen. An order indicates to the newborn screening manager 202 that a physical specimen has been collected and screening results should be provided to the newborn screening manager 202. The order may include a variety of information, such as an identification of the physical specimen, the newborn from which the specimen was collected, one or more parents and/or guardians of the newborn, the place of birth, the place of collection, the time of collection, the testing laboratory, and intended recipients of screening results, for example. In addition, the order may serve to prompt a laboratory, such as the laboratory 208, that screening results should be entered.

An order for newborn screening results may be created either manually or automatically in various embodiments of the present invention. The order may be created manually, for example, by personnel at the hospital 206 accessing the newborn screening manager 202 and entering the order. Alternatively, an order may be automatically generated. For example, the hospital 206 may have a native clinical computing system, which may manage a variety of pieces of clinical information, including newborn information. Upon receipt of newborn information, the native computing system may automatically communicate with the newborn screening manager 202 to create an order.

A physical specimen, such as the physical specimen 216, collected from a newborn is sent to a laboratory, such as the laboratory 208, for testing. As indicated previously, the physical specimen 216 may be identified by a variety of identification means, such as use of an identification number or barcode, for example. Generally, all states maintain at least one state laboratory to perform newborn screening. However, the state laboratories typically only provide testing for a limited number of disorders. As a result, a number of private companies provide testing for a multitude of additional disorders. Accordingly, in some cases, multiple physical specimens from a newborn may be sent to multiple laboratories for testing. As such, it should be understood that although only a single laboratory 208 is shown in FIG. 2, multiple laboratories may be employed for a single newborn within the scope of the present invention. In addition, as noted, the laboratory 208 may represent a state laboratory and/or a private laboratory that provides newborn screening. Further, in some cases, the laboratory 208 may be a part of the hospital 206 where the physical specimen 216 was collected.

After receiving the physical specimen, the laboratory 208 performs the required and/or specified testing, thereby obtaining a number of screening results for the newborn. The laboratory 208 may then access the newborn screening manager 202 and enter the results. As noted above, in some cases, multiple laboratories may perform testing for a single newborn. In such cases, the results from the various laboratories may be aggregated into a single record for the newborn. If an order was previously created for the newborn screening, for instance, at the hospital 206, the newborn screening results are associated with the order. If an order was not previously created, a new profile may be created by the laboratory 208 when entering the newborn screening results.

The newborn screening manager 202 may provide a work queue to the laboratory 208, thereby allowing the laboratory 208 to perform a variety of activities with respect to newborn screening result notification. For example, the work queue may allow the laboratory to view orders that are pending screening results. In some embodiments, an alert may be provided if a screening result has not been entered for an order within a predetermined period of time. In addition, the work queue allows the laboratory 208 to enter newborn screening results and associate the newborn screening results with orders. Although an order will typically include necessary information, such as an identification of recipients for the newborn screening results, in some cases, the laboratory may enter additional information when providing newborn screening results to the newborn screening manager 202. Additionally, for cases in which an order was not previously created, additional information, such as an identification of a recipient, for example, may be entered in conjunction with the newborn screening results. The work queue may further provide a list of results that are pending review by identified recipients. Accordingly, the laboratory 208 may review the list of results pending review and perform any follow-up necessary to ensure that the recipients receive the newborn screening results. In some embodiments, an alert may be provided if a result has not been reviewed by an identified recipient within a predetermined period of time, thereby prompting the laboratory 208 to perform the appropriate efforts to ensure that notification of the newborn screening results is successfully accomplished, such as follow-up by telephone, for example.

In some cases, a state office 210 may be responsible for coordinating the notification of newborn screening results. Accordingly, in such cases, the state office 210 may perform a number of the activities described above with respect to the laboratory 208. For example, the state office 210 may be provided a work queue by the newborn screening manager 202 for managing orders, entering newborn screening results, and/or reviewing newborn screening results that are pending review by an appropriate recipient. In addition, to receive federal grants each year, states are required to report newborn screening information, such as number of births and screening results, for example. As shown in FIG. 2, embodiments of the present invention may facilitate reporting such information to the appropriate federal agency 218.

After receiving newborn screening results, the newborn screening manager 202 may store the results in the associated database 204. The newborn screening manager 202 may then send a notification of the availability of the newborn screening results and/or the actual results to recipients. The recipients may include, for example, the hospital 206, a physician office 214, and a physician, such as a pediatrician identified for the newborn. Recipients for the results may be specified to the newborn screening manager 202 in a number of ways. For example, an initial order for newborn screening may provide an identification of recipients. In addition, the physical specimen may be sent to the laboratory 208 with recipient information, and the laboratory 208 may input such information when entering the newborn screening results. In cases in which a recipient is not specifically indicated, the newborn screening manager 202 may determine a default recipient. For example, the newborn screening manager 202 may assign the healthcare facility that served as the place or birth, such as the hospital 206, as a recipient.

As noted above, in some embodiments, the newborn screening manager 202 may simply deliver the newborn screening results to recipients. By way of example only and not limitation, the delivery of the results may be via an electronic mail message, a client application, or a recipient's native clinical computing system. In other embodiments, the newborn screening manager 202 first provides a notification of the availability of the results to a recipient, and the recipient must then access the results. The notification delivery may likewise be via a number of channels, such as, for example, an electronic mail message, a client application, or a recipient's native clinical computing system.

The newborn screening manager 202 may provide a work queue to recipients for reviewing results. By accessing the work queue, the recipient may view all results that are pending review for that recipient. In some embodiments, an indication may be provided in the work queue for any critical results, which comprise results that include the detection of a disorder. After accessing and viewing results, the recipient may verify that the results have been reviewed. The newborn screening manager 202 may then notify the laboratory 208 and/or state office 210 that the results have been reviewed by the recipient. Additionally or alternatively, the newborn screening manager 202 may automatically remove the reviewed results from the list of results pending review on the work queue for the laboratory 208 and/or state office 210.

In some embodiments, the newborn screening manager 202 may communicate with and populate the newborn screening results into an electronic medical record 212. By way of example only and not limitation, the electronic medical record 212 may comprise a community health record or a personal health record. In some embodiments, the newborn screening manager 202 may map the newborn screening results to genomic concepts in a controlled vocabulary (e.g., an ontology), providing a genetic context for the results. The ontology may in embodiments be or include, for example, an ontology similar to the Clinical Bioinformatics Ontology (CBO) described in the U.S. patent application Ser. No. 11/028,262, which is herein expressly incorporated by reference in its entirety. Such context may be useful for confirmatory tests, which are typically conducted in the event of an abnormal screening result. Additionally, mapping the results to the CBO, for instance, will allow for standardization of discreet results between states and across organizations. For example, a positive screening result for phenylketonuria (PKU) can be mapped as a phenotypic result for the patient in a CBO. Because the results are captured in a regional repository, they are ideally positioned to become the first elements of a personal genomic record. Later genetic test results can be added to a person's genomic record, gradually fleshing out the information that is known about the individual during his/her lifetime. Collectively, these results can contribute to haplotype logic and the inference of other results, for example, by processing the results similar to that described in the U.S. patent application Ser. No. 10/751,292, which is herein expressly incorporated by reference in its entirety.

Figure 3:
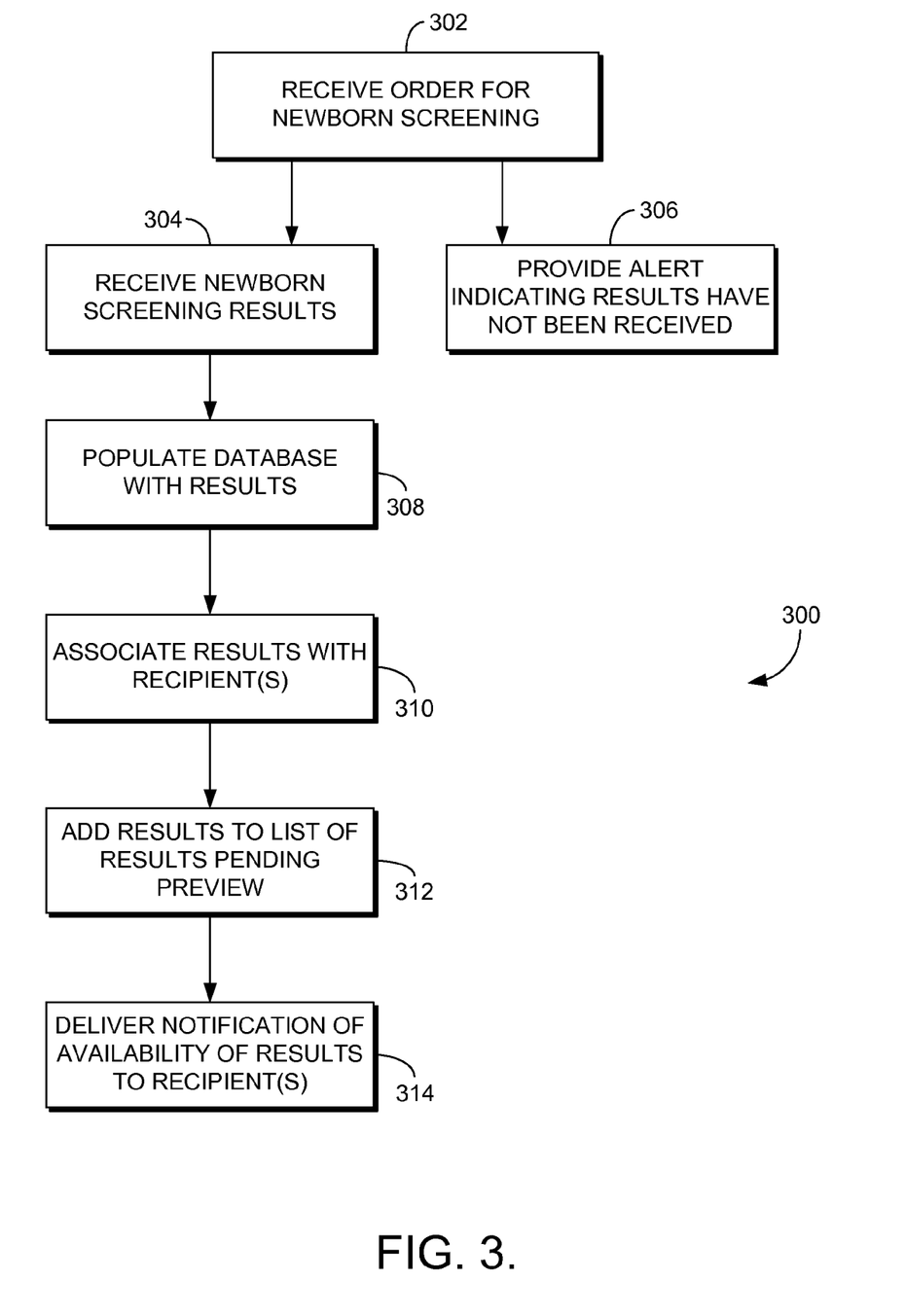
FIG. 3 is a flow diagram showing a method for receiving newborn screening results and notifying a recipient of the availability of the results in accordance with an embodiment of the present invention.

Referring now to FIG. 3, a flow diagram is provided illustrating a method 300 for receiving newborn screening results and providing notification of the results in accordance with an embodiment of the present invention. Initially, as shown at block 302, a newborn screening manager, such as the newborn screening manager 202 of FIG. 2, receives an order for newborn screening. As discussed previously, a healthcare facility, such as the hospital 206 of FIG. 2, may collect a physical specimen and enter an order for newborn screening. The order may indicate that a physical specimen has been collected and that newborn screening results are to be provided for the order. In addition, the order may include a variety of pieces of information, such as an identification of the physical specimen, the newborn from which the specimen was collected, one or more parents and/or guardians of the newborn, the place of birth, the place of collection, the time of collection, the testing laboratory, and intended recipients of screening results, for example.

The healthcare facility sends the physical specimen to a laboratory, which after receiving the physical specimen performs the testing process and enters results into the newborn screening manager. Accordingly, as shown at block 304 of FIG. 3, the newborn screening manager receives the newborn screening results. However, in some cases, the newborn screening results for the order may not be received within a predetermined period of time. In such cases, an alert may be provided, as shown at block 306. The alert may be delivered to a variety of entities within the scope of the present invention. For example, the alert may be delivered to the laboratory indicated as performing the screening, a state office, the healthcare facility that entered the order, and/or any designated recipients.

As shown at block 308, the newborn screening manager populates the newborn screening results into an associated database, such as the database 204 of FIG. 2. In addition, the newborn screening results may be associated with one or more recipients, such as a hospital, physician office, or physician, as shown at block 310 of FIG. 3. If a recipient has an associated list of results to be reviewed, the current results are added to the recipient's list. The recipients may be identified, for instance, by the original order, by information provided when the results are entered, or by default rules. The newborn screening results may further be added to a list of results pending review such that a laboratory and/or state office may monitor the notification process, as shown at block 312. A notification of the availability of the newborn screening results may then be delivered to each identified and/or default recipient of the results, as shown at block 314. As discussed previously, any means of communication may be provided for the delivery of the notification, including, for instance, an electronic mail message, a message via a client application communicating with the newborn screening manager, and a message via a native clinical computing system communicating with the newborn screening manager.

Figure 4:
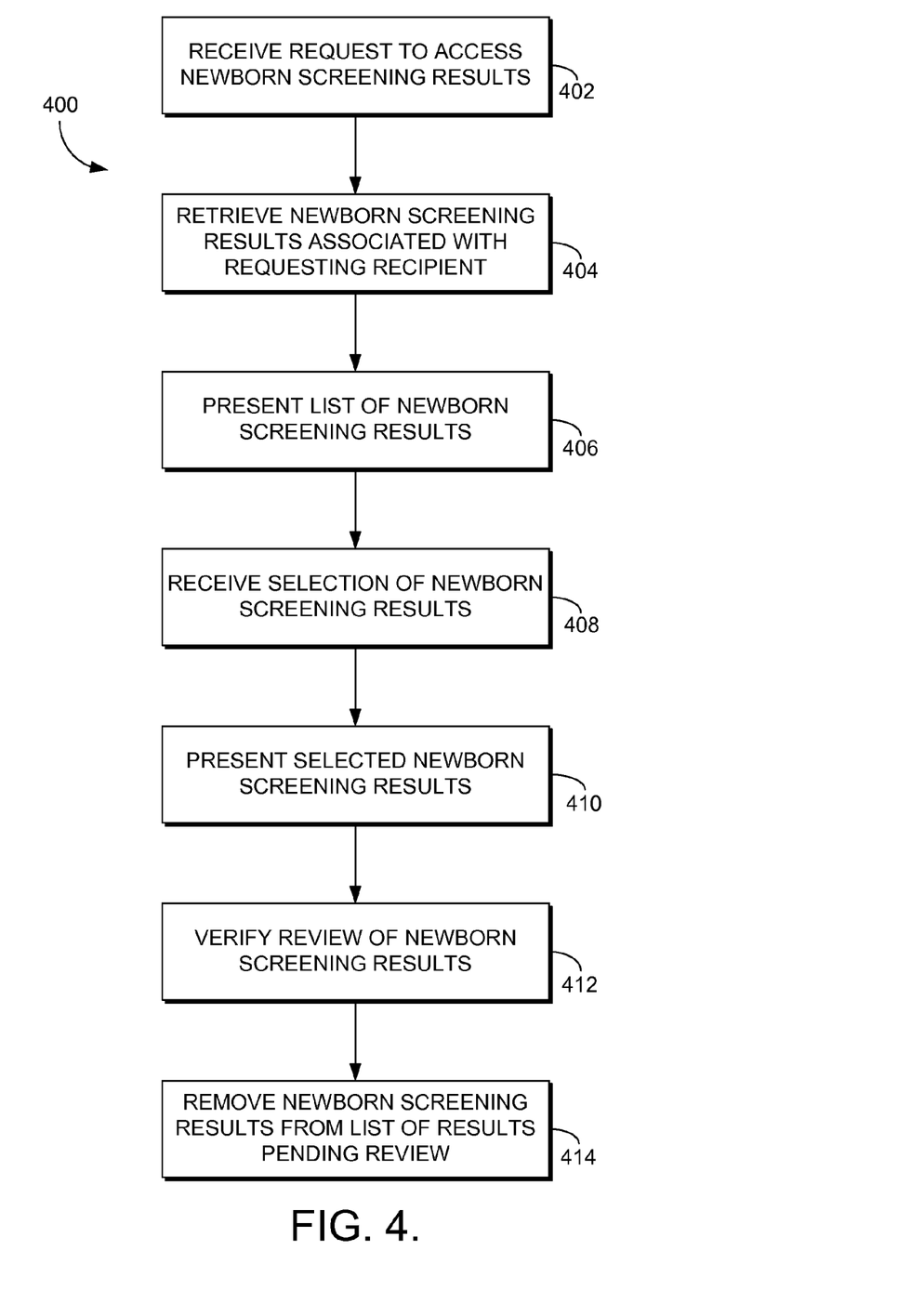
FIG. 4 is a flow diagram showing a method for providing a recipient access to newborn screening results in accordance with an embodiment of the present invention.

Turning to FIG. 4, a flow diagram is provided illustrating a method 400 for providing a recipient access to newborn screening results and verifying that the results have been reviewed by the recipient. Initially, as shown at block 402, a request to access newborn screening results is received from a recipient. The request may include a secure log-in process for privacy purposes. In response to the request, all newborn screening results associated with the recipient are retrieved, as shown at block 404. The list of newborn screening results is then presented to the recipient, as shown at block 406. In some embodiments, an indication may be provided for any critical results, such that the recipient may readily identify these results for follow-up.

The recipient may review the list of newborn screening results and select to review results for a particular newborn, as shown at block 408. The selected newborn screening results are then presented to the recipient, as shown at block 410, with any other relevant information. Review of the newborn screening results may then be verified, as shown at block 412. In some embodiments, the verification may be automatic when the results are selected and presented. In other embodiments, the recipient may be required to manually verify that the results have been reviewed. After verifying that the set of newborn screening results have been reviewed by the recipient, the set of newborn screening results may be removed from the laboratory's list and/or state office's list of results pending review, as shown at block 414.

Figure 5:
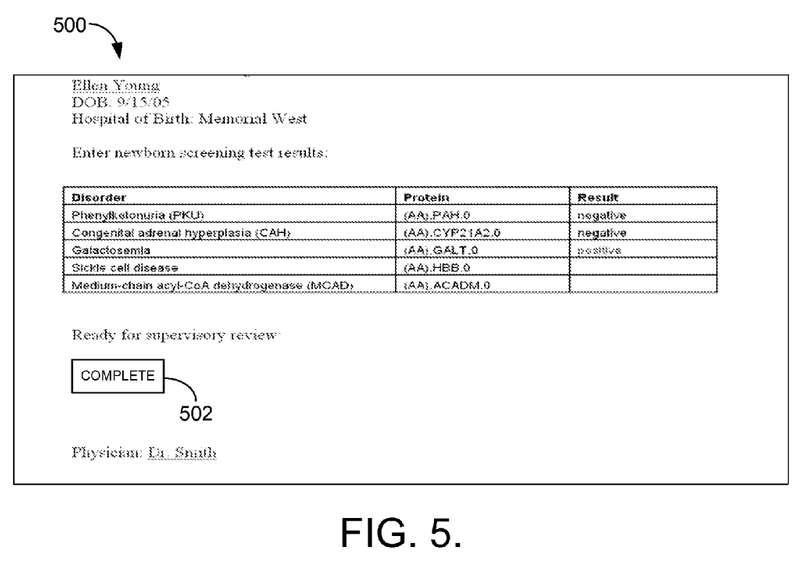
FIG. 5 is an illustrative screen display showing a work queue for entering newborn screening results in accordance with an embodiment of the present invention.
Figure 6:
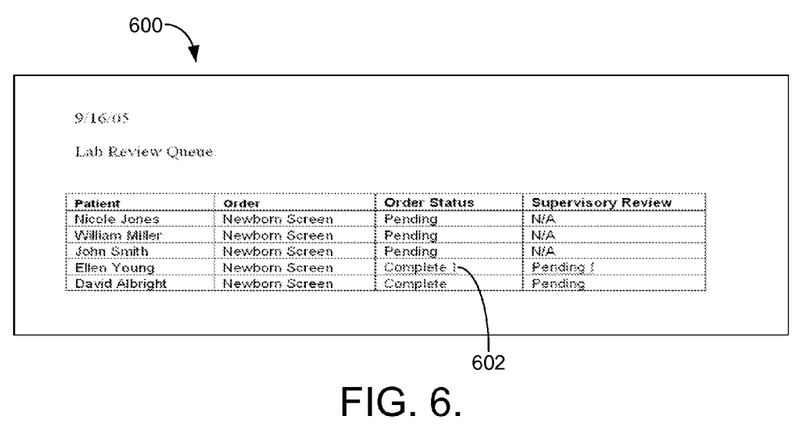
FIG. 6 is an illustrative screen display showing a work queue for reviewing pending newborn screening orders in accordance with an embodiment of the present invention.
Figure 7:
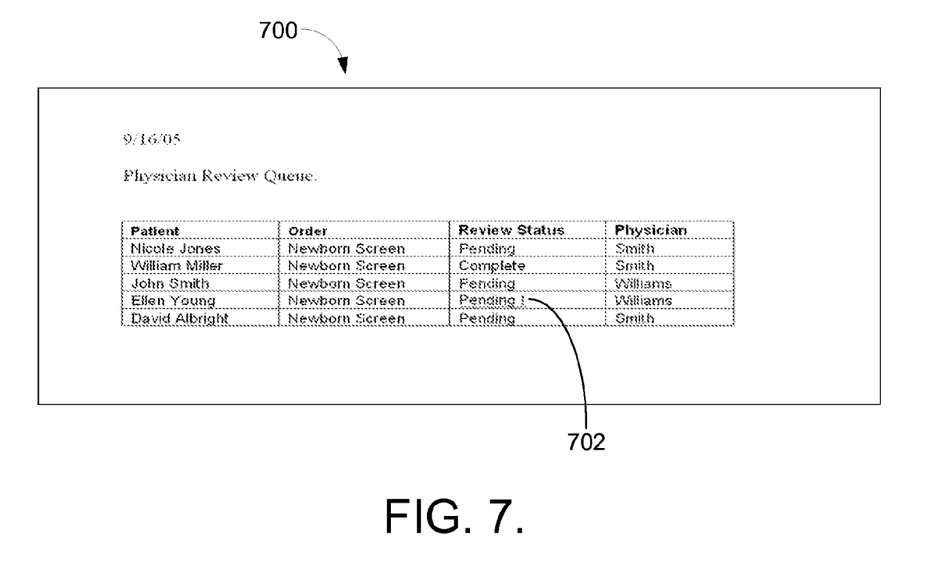
FIG. 7 is an illustrative screen display showing a work queue for determining whether recipients of newborn screening results have accessed and reviewed the results in accordance with an embodiment of the present invention.

Referring now to FIG. 5 through FIG. 7, exemplary screen displays are provided illustrating work queues that may be provided to a laboratory and/or state office for managing newborn screening results in accordance with embodiments of the present invention. It will be understood and appreciated by those of ordinary skill in the art that the screen displays of FIG. 5 through FIG. 7 are provided by way of example only and are not intended to limit the scope of the present invention in any way. Referring initially to FIG. 5, an exemplary screen display 500 of a work queue for entering newborn screen results is illustrated. As shown in FIG. 5, the work queue allows a user, such as a laboratory technician, for instance, to enter results of newborn screening performed for a particular newborn. The work queue may include a variety of pieces of information, such as the name of the newborn, the date of birth, the hospital of birth, and an associated physician. In some embodiments, the work queue will automatically include those disorders tested by the particular laboratory. In other embodiments, the user may be able to enter the various disorders tested. The work queue may allow the user to enter results by providing an indication as to whether the result for each disorder was positive or negative. After entering the results for the various disorders tested, a user may complete the newborn screening results by selecting the complete button 502. In some embodiments, supervisory review of the results may be required after the results are entered.

Referring now to FIG. 6, an exemplary screen display 600 of a work queue for reviewing newborn screening orders is provided. The work queue shown in FIG. 6 allows a laboratory and/or state office to review newborn screening orders that are pending results and/or supervisory review of entered results. As shown in FIG. 6, the work queue may list the orders by patient (i.e., newborn) and provide an indication as to whether the results for each order are pending or have been entered. In embodiments in which supervisory review is required, the work queue may also provide an indication as to whether the results for each order are pending review. In some embodiments, an indication may be provided in the work queue, such as the alert icon 602, for orders in which results have been entered that include a critical result.

A work queue may also be provided to a laboratory and/or state office to track whether newborn screening results have been accessed by a recipient of the results. An exemplary screen display 700 of such a work queue is shown in FIG. 7. As shown in FIG. 7, the work queue may list the newborn screening results by patient (i.e., newborn). The recipient for each set of newborn screening results may also be provided. Further, an indication is provided regarding whether each set of newborn screening results is pending review by the indicated recipient or whether each has been reviewed. In some embodiments, an indication may also be provided, such as the alert icon 702, for instance, for newborn screening results that include a critical result.

As discussed previously, after newborn screening results have been entered by a laboratory and/or state office, a notification may be provided to a recipient, who may then access and verify review of the results. An example of a recipient being notified of the availability of newborn screening results and accessing the results will now be discussed with reference to the screen displays of FIG. 8. through FIG. 11. It will be understood and appreciated by those of ordinary skill in the art that the screen displays of FIG. 8 through FIG. 11 are provided by way of example only and are not intended to limit the scope of the present invention in any way. As shown in the FIG. 8, the recipient, Dr. Smith, receives an electronic mail message indicating that a newborn screening result is ready for review. The message also indicates that the results include a critical test result, indicating that a disorder was detected by the screening. The message also includes a link 802 to a web-based site to access the newborn screening results.

By selecting the link 802, the recipient may navigate to the web-based site to access the newborn screening results. As shown in the screen display of FIG. 9, the recipient may be required to login to access the newborn screening results. After logging in, a list of newborn screening results associated with the recipient is presented, as shown in the screen display of FIG. 10. The list may provide a variety of information, such as, for instance, a patient (e.g., a newborn), a date of result, and a hospital. Other information may be provided within the scope of the present invention. In addition, an indication such as the alert icon 1002 may be provided to indicate the presence of a critical result. The recipient may review the list of newborn screening results and select a particular set of results for review. For example, the recipient may select to view the results for Jane Doe. Based on the selection, the newborn screening results associated with Jane Doe may be presented as shown in the screen display of FIG. 11. The presentation of the results may include additional information, such as information regarding a critical result detected. After reviewing the results, the recipient may verify that the results have been reviewed by selecting the verify button 1102.

Figure 8:
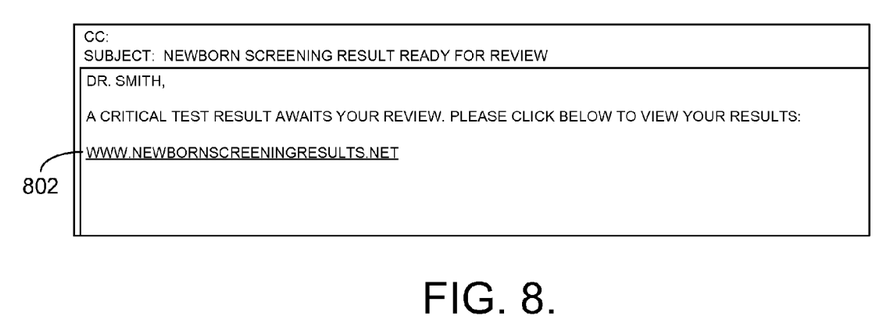
FIG. 8 is an illustrative screen display showing an electronic mail message notifying a recipient of the availability of newborn screening results in accordance with an embodiment of the present invention.
Figure 9:
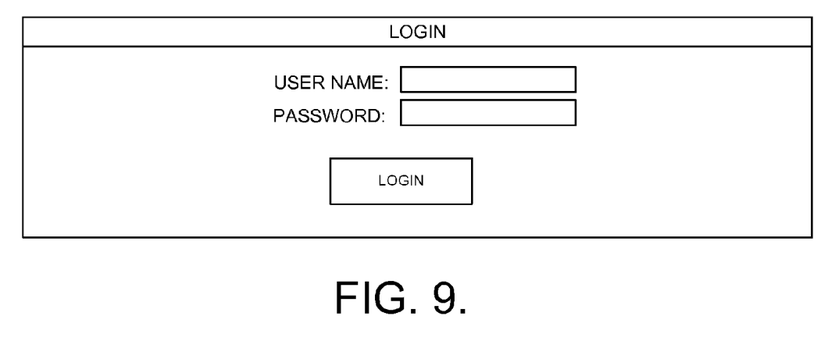
FIG. 9 is an illustrative screen display showing a secure login for a recipient to access newborn screening results in accordance with an embodiment of the present invention.
Figure 10:
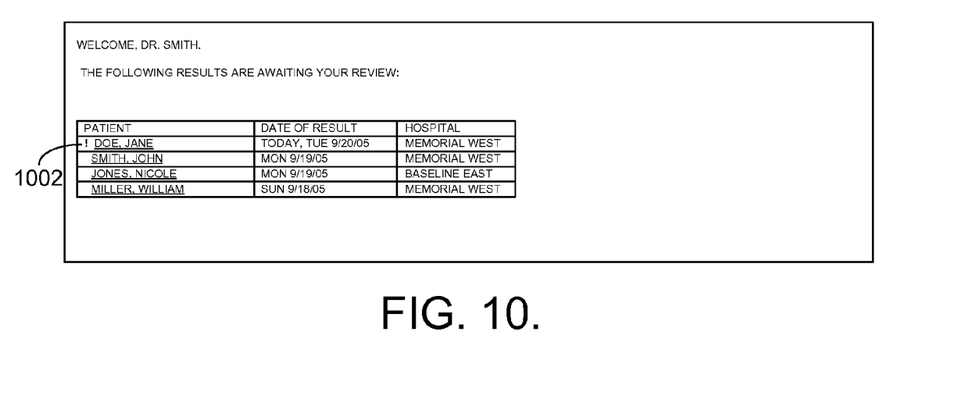
FIG. 10 is an illustrative screen display providing a list of newborn screening results available for review by a recipient in accordance with an embodiment of the present invention.
Figure 11:
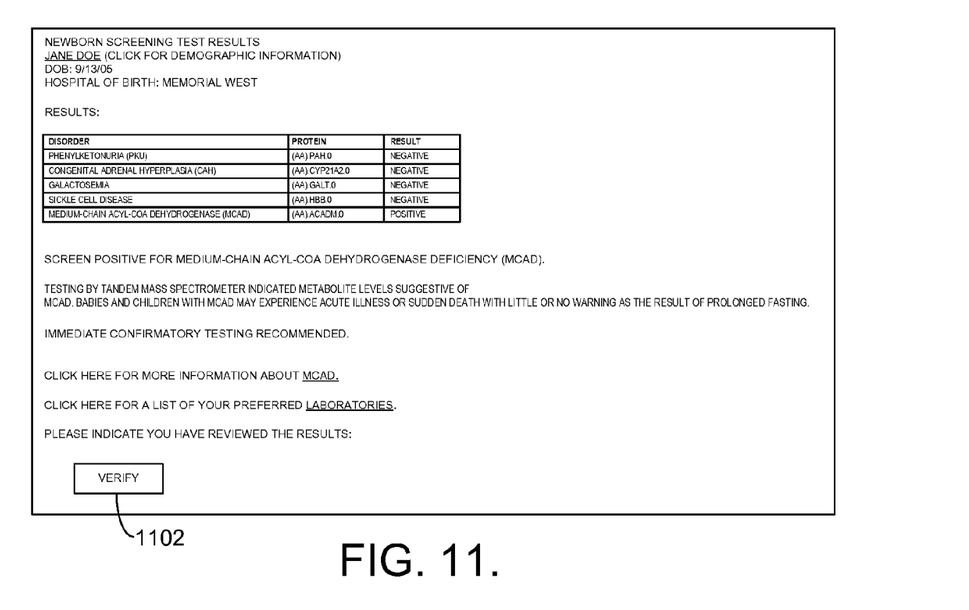
FIG. 11 is an illustrative screen display presenting selected newborn screening results to a recipient in accordance with an embodiment of the present invention.

Although the notification of newborn screening results shown in FIG. 8 and described above is via an electronic mail message, as described previously, other forms of notification may be provided within the scope of the present invention, such as, for instance, a message provided via a client application or a native clinical computing system communicating with a newborn screening manager. Similarly, although a web-based access to the newborn screening results is shown and described with reference to FIG. 8 through FIG. 11, as discussed previously, different ways of accessing newborn screening results are contemplated within the scope of the present invention, including, for instance, via a client application or native clinical computing system communicating with a newborn screening manager.

As can be understood, embodiments of the present invention provide computerized systems and methods for collecting and reporting newborn screening results to recipients. The present invention has been described in relation to particular embodiments, which are intended in all respects to be illustrative rather than restrictive. Alternative embodiments will become apparent to those of ordinary skill in the art to which the present invention pertains without departing from its scope.

From the foregoing, it will be seen that this invention is one well adapted to attain all the ends and objects set forth above, together with other advantages which are obvious and inherent to the system and method. It will be understood that certain features and subcombinations are of utility and may be employed without reference to other features and subcombinations. This is contemplated and within the scope of the claims.

What is claimed is:

1. One or more non-transitory computer-storage media storing computer-useable instructions that, when used by one or more computing devices, cause the one or more computing devices to perform a method in a clinical computing environment for communicating a newborn screening result to one or more recipients, the method comprising:
receiving a newborn screening result at a newborn screening manager, wherein the newborn screening manager is configured to communicate with at least one of a state laboratory performing newborn screening and a state office responsible for coordinating newborn screening results;
storing the newborn screening result;
identifying one or more recipients of the newborn screening result;
communicating the newborn screening result to the one or more recipients by:
providing a notification of an availability of the newborn screen result to the one or more recipients,
receiving, from at least one of the one or more recipients, a request to access the newborn screening result, and
communicating the newborn screening result to the at least one of the one or more recipients based on the request;
determining that the newborn screening result has not been accessed by at least one of the one or more recipients within a predetermined period of time after providing the notification of the availability of the newborn screening result;
generating an alert notification based on determining that the newborn screening result has not been accessed within the predetermined period of time; and communicating the alert notification to at least one selected from the following: the state laboratory and the state office.

2. The one or more non-transitory computer-storage media of claim 1, further comprising receiving an order for a newborn screening.

3. The one or more non-transitory computer-storage media of claim 2, wherein the order comprises an identification for at least one of a physical specimen associated with the newborn screening, a newborn, one or more parents of a newborn, one or more guardians of a newborn, a place of birth, a place of collection, a time of collection, a testing laboratory, and one or more recipients of the newborn screening result.

4. The one or more non-transitory computer-storage media of claim 2, further comprising associating the newborn screening result with the order for the newborn screening.

5. The one or more non-transitory computer-storage media of claim 2, further comprising generating an alert notification if the newborn screening result is not received within a predetermined period of time after receiving the order for the newborn screening.

6. The one or more non-transitory computer-storage media of claim 1, further comprising adding the newborn screening result to a list of newborn screening results pending review by a recipient; and communicating the list of newborn screening results pending review by a recipient to at least one of following: the state laboratory and the state office.

7. The one or more non-transitory computer-storage media of claim 6, further comprising receiving a verification that the newborn screening result has been reviewed by at least one of the one or more recipients.

8. The one or more non-transitory computer-storage media of claim 7, further comprising removing the newborn screening result from the list of newborn screening results pending review based on the verification.

9. The one or more non-transitory computer-storage media of claim 1, further comprising populating the newborn screening result into at least one of a community health record, a personal health record, and an electronic medical record.

10. The one or more non-transitory computer-storage media of claim 1, further comprising associating the newborn screening result with a controlled vocabulary.

11. The one or more non-transitory computer-storage media of claim 10, wherein the controlled vocabulary comprises an ontology.

12. The one or more non-transitory computer-storage media of claim 1, further comprising:
determining if the newborn screening result is a critical result; and
if the newborn screening result is determined to be a critical result, providing an alert indication that the newborn screening result is a critical result.

13. One or more non-transitory computer-storage media storing computer-useable instructions that, when used by one or more computing devices, cause the one or more computing devices to perform a method in a clinical computing environment for facilitating the notification of an availability of a newborn screening result, the method comprising:
receiving a newborn screening result;
adding the newborn screening result to a list of newborn screening results pending review;
providing a notification of an availability of the newborn screening result to one or more recipients;
providing the list of newborn screening results pending review to at least one of a state laboratory performing newborn screening and a state office responsible for coordinating newborn screening results
determining that the newborn screening result has not been accessed by at least one of the one or more recipients within a predetermined period of time after providing the notification of the availability of the newborn screening result;
generating an alert notification based on determining that the newborn screening result has not been accessed within the predetermined period of time; and
communicating the alert notification to at least one selected from the following: the state laboratory and the state office.

14. The one or more non-transitory computer-storage media of claim 13, further comprising receiving a verification that the newborn screening result has been reviewed by at least one of the one or more recipients.

15. The one or more non-transitory computer-storage media of claim 14, further comprising removing the newborn screening result from the list of newborn screening results pending review based on the verification.

16. One or more non-transitory computer-storage media storing computer-useable instructions that when used by one or more first computing devices cause the one or more first computing devices to perform a method for facilitating the collection and dissemination of newborn screening results, the method comprising:
receiving a plurality of orders for newborn screening results;
communicating at least one first work queue to one or more second computing devices of a testing laboratory, the at least one first work queue allowing laboratory personnel to view orders pending entry of newborn screening results, the first work queue also allowing laboratory personnel to enter newborn screening results;
receiving newborn screening results via the at least one first work queue;
associating the newborn screening results with corresponding orders;
storing the newborn screening results in a central database;
providing an electronic notification of availability of newborn screening results to recipients associated with the orders;
providing access to the newborn screening results in the central database when requested by recipients;
automatically tracking whether recipients have accessed newborn screening results from the central database;
determining that a first newborn screening result has not been accessed by at least one recipient within a predetermined period of time after providing notification of availability of the first newborn screening result;
generating an alert notification based on determining that the first newborn screening result has not been accessed within the predetermined period of time;
communicating the alert notification to at least one selected from the following: a state laboratory and a state office ; and
communicating at least one second work queue to one or more third computing devices of the state office responsible for a newborn screening program, the second work queue allowing state personnel to view newborn screening results pending review by a recipient.

* * * * *